United States Patent [19]

Reichmann

[11] Patent Number: 4,885,427
[45] Date of Patent: Dec. 5, 1989

[54] ISOMERIZATION OF UNEXTRACTED, ETHYLBENZENE-CONTAINING XYLENE STREAMS USING A CATALYST MIXTURE CONTAINING MOLYBDENUM ON SILICA AND SUPPORTED CRYSTALLINE BOROSILICATE MOLECULAR SIEVE

[75] Inventor: Mark G. Reichmann, Oak Park, Ill.

[73] Assignee: Amoco Corporation, Chicago, Ill.

[21] Appl. No.: 250,950

[22] Filed: Sep. 29, 1988

[51] Int. Cl.$^4$ ................................................ C07C 5/22
[52] U.S. Cl. ..................................... 585/480; 585/481
[58] Field of Search ................................. 585/480, 481

[56] References Cited

U.S. PATENT DOCUMENTS 4,202,996  5/1980  Hilfman ............................... 585/477

Primary Examiner—Curtis R. Davis
Attorney, Agent, or Firm—Reed F. Riley; William H. Magidson; Ralph C. Medhurst

[57] ABSTRACT

Described are catalyst mixtures comprising a HAMS-1B crystalline borosilicate molecular sieve incorporated into an inorganic matrix component and a molybdenum on silica component. These mixtures when used to isomerize unextracted xylene streams containing ethylbenzene to mixtures rich in paraxylene demonstrate improved paraffins and naphthenes conversion to light hydrocarbons and convert most of the ethylbenzene by a hydrodeethylation mechanism to benzene and ethane.

7 Claims, No Drawings

ISOMERIZATION OF UNEXTRACTED, ETHYLBENZENE-CONTAINING XYLENE STREAMS USING A CATALYST MIXTURE CONTAINING MOLYBDENUM ON SILICA AND SUPPORTED CRYSTALLINE BOROSILICATE MOLECULAR SIEVE

BACKGROUND OF THE INVENTION

This invention relates to xylene isomerization catalyst mixtures based upon supported AMS-1B crystalline, borosilicate molecular sieve catalyst compositions, and particularly, to isomerization of an unextracted, ethylbenzene-containing xylene stream using such mixtures, which process converts ethylbenzene to benzene and ethane primarily by hydrodeethylation and has improved paraffins and naphthenes conversion. More particularly, it relates to catalyst mixtures comprising an AMS-1B crystalline, borosilicate molecular sieve incorporated into an inorganic matrix and silica-supported molybdenum and to processes for using these catalyst mixtures to isomerize an unextracted, ethylbenzene-containing xylene stream to a mixture rich in paraxylene in a process which shows improved paraffins and naphthenes conversion to light hydrocarbons and converts ethylbenzene primarily by hydrodeethylation to benzene and ethane.

Typically, paraxylene is derived from mixtures of $C_8$ aromatics separated from such raw materials as petroleum naphthas, particularly reformates, usually by isomerization followed by, for example, lower-temperature crystallization of the paraxylene with recycle of the crystallizer liquid phase to the isomerizer. Principal raw materials are catalytically reformed naphthas and petroleum distillates. The fractions from these sources that contain $C_8$ aromatics vary quite widely in composition but will usually contain 10 to 35 weight percent ethylbenzene and up to about 10 weight percent primarily $C_9$ paraffins and naphthenes with the remainder being primarily xylenes divided approximately 50 weight percent meta, and 25 percent each of the ortho and para isomers. The primarily $C_9$ paraffins and naphthenes can be removed substantially by extraction to produce what are termed "extracted" xylene feeds, however, the extraction step adds to processing costs. Feeds that do not have the primarily $C_9$ paraffins and naphthenes removed by extraction are termed "unextracted" xylene feeds.

The ethylbenzene in a xylene mixture is very difficult to separate from the other components due to similar volatility, and, if it can be converted during isomerization to products more readily separated from the xylenes, buildup of ethylbenzene in the recycle loop is prevented and process economics are greatly improved. The primarily $C_9$ paraffins and naphthenes present in unextracted feeds unless removed also build up in the recycle loop and are usually extracted prior to isomerization as most commercial isomerization processes do not provide a catalyst which effectively converts them to easily separable-by-distillation products. Thus, it would be valuable to have a catalyst/process for xylene isomerization which would effectively convert both the ethylbenzene and primarily $C_9$ paraffins and naphthenes to easily separable products without affecting the isomerization efficiency. In addition, the catalyst should minimize xylene loss via hydrogenation and cracking.

Xylene isomerization catalysts can be classified into three types based upon the manner in which they convert ethylbenzene: (1) naphthene pool catalysts, (2) transalkylation catalysts, and (3) hydrodeethylation catalysts.

Naphthene pool catalysts are capable of converting a portion of the ethylbenzene to xylenes via naphthene intermediates. These catalysts contain a strong hydrogenation function, such as platinum, and an acid function, such as chlorided alumina, amorphous silica-alumina, or a molecular sieve. The role of the hydrogenation function in these catalysts is to hydrogenate the $C_8$ aromatics to establish essentially equilibrium between the $C_8$ aromatics and the $C_8$ cyclohexanes. The acid function interconverts ethylcyclohexane and the dimethylcylohexanes via cyclopentane intermediates. These $C_8$ cycloparaffins form the so-called naphthene pool.

It is necessary to operate naphthene pool catalysts at conditions that allow the formation of a sizable naphthene pool to allow efficient conversion of ethylbenzene to xylenes. Unfortunately, naphthenes can crack on the acid function of the catalyst, and the rate of cracking increases with the size of the naphthene pool. Naphthene cracking leads to high xylene loss, and the by-products produced by naphthene cracking are low-valued paraffins. Thus, naphthene pool catalysts are generally less economic than the transalkylation-type and hydrodee- thylation-type catalysts.

The transalkylation catalysts generally contain a shape selective molecular sieve. A shape selective catalyst is one that prevents some reactions from occurring based on the size of the reactants, products, or intermediates involved. In the case of common transalkylation catalysts, the molecular sieve contains pores that are apparently large enough to allow ethyl transfer to occur via a dealkylation/realkylation mechanism, but small enough to substantially suppress methyl transfer which requires the formation of a bulky biphenylalkane intermediate. The ability of transalkylation catalysts to catalyze ethyl transfer while suppressing methyl transfer allows these catalysts to convert ethylbenzene while minimizing xylene loss via xylene disproportionation.

When ethyl transfer occurs primarily by dealkylation/realkylation, it is possible to intercept and hydrogenate the ethylene intermediate involved with this mechanism of ethyl transfer by adding a hydrogenation function to the catalyst. The primary route for converting ethylbenzene then becomes hydrodeethylation, which is the conversion of ethylbenzene to benzene and ethane. It is desirable to selectively hydrogenate the ethylene intermediate without hydrogenating aromatics (without establishing a naphthene pool) to prevent the cracking of the naphthenes that occurs over the acid function of the catalyst. Commercial hydrodeethylation catalysts selectively hydrogenate ethylene without substantial hydrogenation of aromatics at reported commercial conditions.

In order to form a hydrodeethylation catalyst, it is essential to use an acidic component that behaves as a shape selective catalyst, i.e., one that suppresses the formation of the bulky biphenylalkane intermediate required for transmethylation, because transethylation can occur via a similar intermediate. For catalysts with pores large enough to allow the formation of these biphenylalkane intermediates, transethylation appears to occur primarily via these intermediates. In this case, ethylene is not an intermediate for transethylation, and the addition of a hydrogenation component cannot produce a hydrodeethylation catalyst Molecular sieves such as the AMS-1B crystalline, borosilicate molecular sieves have shown great utility in the isomerization of xylenes to make primarily paraxylene Such sieves when supported on an oxide carrier like alumina effectively produce equilibrium amounts of paraxylene and dispose of ethylbenzene largely by transalkylation without serious loss of xylenes. However, such sieves are not very effective in removing paraffins and naphthenes during the isomerization of xylenes and they are generally used with extracted feeds.

Periodic Group VIb elements including molybdenum have shown utility in the past for various hydrocarbon conversions including hydrogenation. In particular, in U.S. Pat. Nos. 4,420,467; 4,532,226; and 4,655,255, molybdenum is said to be incorporated into or on a molecular sieve framework, which sieve is useful for hydrocarbon conversions including isomerization. In U.S. Pat. No. 4,202,996, hydrocarbon isomerization is carried out over a catalytic composite having a nickel component, a molybdenum component, a platinum component in combination with a zeolitic carrier. In other work, the activity of supported molybdenum compounds useful for hydrogenation/dehydrogenation has been found to depend upon the oxidation state of molybdenum with the lower molybdenum oxidation states being more effective.

Now it has been found that by adding molybdenum on silica to an alumina-supported HAMS-1B crystalline, borosilicate molecular sieve catalyst composition, a catalyst mixture is formed which, when used for xylene isomerization of unextracted xylene streams, removes ethylbenzene primarily by the hydrodeethylation mechanism to benzene and ethane and can substantially increase the removal of paraffins and naphthenes by cracking to light hydrocarbons. These results are obtained, moreover, without otherwise substantially affecting the isomerization effectiveness of the supported molecular sieve catalyst composition. Unexpectedly, other common molybdenum supports such as alumina do not produce a supported molybdenum which is as effective in removing paraffins and naphthenes when made into a catalyst mixture with the borosilicate sieve.

SUMMARY OF THE INVENTION

Described herein is a vapor phase process comprising isomerizing in the presence of hydrogen an unextracted xylene stream containing a major amount of xylene and a minor amount of ethylbenzene to a mixture rich in paraxylene over a catalyst mixture containing a HAMS-1B crystalline, borosilicate molecular sieve incorporated into alumina component and a molybdenum on silica component, said molybdenum on silica component containing between about 1 and about 20 weight percent molybdenum calculated as the metal, said catalyst mixture containing between about 5 to about 95 percent by weight of said molybdenum on silica component based upon the total weight of said mixture, and said HAMS-1B crystalline, borosilicate molecular sieve incorporated in alumina component containing between about 40 and about 95 weight percent alumina.

DETAILED DESCRIPTION OF THE INVENTION

Unextracted xylene-containing feeds to this process include one or more of the xylene isomers and between about five and about thirty-five weight percent of ethylbenzene depending upon the source of feed. These feeds also include between about one and about ten percent primarily $C_9$ paraffins and naphthenes. Such paraffins and naphthenes include materials such as n-nonane, methyl octanes, dimethylheptanes, trimethylcyclohexane, ethylmethylcyclohexane and the like.

The catalyst mixtures used in this invention include an AMS-1B crystalline borosilicate molecular sieve which is described in U.S. Pat. Nos. 4,268,420; 4,269,813; and 4,285,919, and Published European Patent Application 68,796, all of which are incorporated herein by reference. AMS-1B crystalline borosilicate generally can be characterized by the X-ray pattern listed in Table A and by the composition formula:

$$0.9 \pm 0.2 M_{2/n}O:B_2O_3:ySiO_2:zH_2O$$

wherein M is at one cation, n is the oxidation state of the cation, y is between 4 and about 600 and z is between 0 and about 160.

TABLE A

| d-Spacing Å (1) | Assigned Strength (2) |
|---|---|
| 11.2 ± 0.2 | W-VS |
| 10.0 ± 0.2 | W-MS |
| 5.97 ± 0.07 | W-M |
| 3.82 ± 0.05 | VS |
| 3.70 ± 0.05 | MS |
| 3.62 ± 0.05 | M-MS |
| 2.97 ± 0.02 | W-M |
| 1.99 ± 0.02 | VW-M |

(1) Copper K alpha radiation
(2) VW = very weak; W = weak; M = medium; MS = medium strong; VS = very strong The AMS-1B borosilicate molecular sieve useful in this invention can be prepared by crystallizing an aqueous mixture, at a controlled pH, of sources for cations, an oxide of boron, an oxide of silicon, and an organic template compound.

Typically, the mol ratios of the various reactants can be varied to produce the crystalline borosilicates of this invention. Specifically, the mol ratios of the initial reactant concentrations are indicated below:

|  | Broad | Preferred | Most Preferred |
|---|---|---|---|
| $SiO_2/B_2O_3$ | 5-400 | 10-150 | 10-80 |
| $R_2O^+/[R_2O^+ + M_{2/n}O]$ | 0.1-1.0 | 0.2-0.97 | 0.3-0.97 |
| $OH^-/SiO_2$ | 0.01-11 | 0.1-2 | 0.1-1 |
| $H_2O/OH^-$ | 10-4000 | 10-500 | 10-500 | wherein R is an organic compound and M is at least one cation having the oxidation state n, such as an alkali or an alkaline earth metal cation or hydrogen. By regulation of the quantity of boron (represented as $B_2O_3$) in the reaction mixture, it is possible to vary the $SiO_2/B_2O_3$ molar ratio in the final product.

More specifically, the material useful in the present invention is prepared by mixing a base, a boron oxide source, and an organic template compound in water (preferably distilled or deionized). The order of addition usually is not critical, although a typical procedure is to dissolve base and boric acid in water and then add the template compound. Generally, the silicon oxide compound is added with intensive mixing such as that performed in a Waring Blender and the resulting slurry is transferred to a closed crystallization vessel for a suitable time. After crystallization, the resulting crystalline product can be filtered, washed with water, dried, and calcined.

During preparation, acidic conditions should be avoided. When alkali metal hydroxides are used, the values of the ratio of $OH^-/SiO_2$, shown above, should furnish a pH of the system that broadly falls within the range of about 9 to about 13.5. Advantageously, the pH of the reaction system falls within the range of about 10.5 to about 11.5 and most preferably between about 10.8 and about 11.2.

Examples of materials affording silicon oxide useful in this invention include silicic acid, sodium silicate, tetraalkyl silicates and Ludox, a stabilized polymer of silicic acid manufactured by E. I. DuPont de Nemours & Co. Typically, the oxide of boron source is boric acid although equivalent species can be used such as sodium borate and other boron-containing compounds.

Cations useful in formation of AMS-1B crystalline borosilicate include hydrogen ion, the cationic form of the organic template, alkali metal and alkaline earth metal cations such as sodium, potassium, lithium, calcium, and magnesium. Ammonium cations may be used alone or in conjunction with such metal cations. Since basic conditions are required for crystallization of the molecular sieve of this invention, the source of such cation can be a hydroxide such as sodium hydroxide. Alternatively, AMS-1B can be prepared directly and more preferably in the hydrogen form by replacing such metal cation hydroxides with an organic base such as ethylenediamine as described in Published European Application No. 68,796.

Organic templates useful in preparing AMS-1B crystalline borosilicate include alkylammonium cations or precursors thereof such as tetraalkylammonium compounds, especially tetra-n-propylammonium compounds. A useful organic template is tetra-n-propylammonium bromide. Diamines, such as hexamethylenediamine, can be used.

In a more detailed description of a typical preparation of this invention, suitable quantities of sodium hydroxide and boric acid ($H_3BO_3$) are dissolved in distilled or deionized water followed by addition of the organic template. The pH may be adjusted between about 11.0 ±0.2 using a compatible acid or base such as sodium bisulfate or sodium hydroxide. After sufficient quantities of a silica source such as a silicic acid polymer (Ludox) are added with intensive mixing, preferably the pH is again checked and adjusted to a range of about 11.0±0.2.

Alternatively and more preferably, AMS-1B crystalline borosilicate molecular sieve can be prepared by crystallizing a mixture of sources for an oxide of silicon, an oxide of boron, an alkylammonium compound and ethylenediamine such that the initial reactant molar ratios of water to silica range from about 5 to about 25, preferably about 5 to about 20 and most preferably from about 10 to about 15. In addition, preferable molar ratios for initial reactant silica to oxide of boron range from about 4 to about 150, more preferably from about 5 to about 80 and most preferably from about 5 to about 20. The molar ratio of ethylenediamine to silicon oxide should be above about 0.05, typically below 5, preferably between about 0.1 and about 1.0, and most preferably between about 0.2 and about 0.5. The molar ratio of alkylammonium compound, such as tetra-n-propylammonium bromide, to silicon oxide can range from 0 to about 1 or above, typically above about 0.005, preferably about 0.01 to about 0.1, more preferably about 0.01 to about 0.1, and most preferably about 0.02 to about 0.05.

The resulting slurry is transferred to a closed crystallization vessel and reacted usually at a pressure at least the vapor pressure of water for a time sufficient to permit crystallization which usually is about 0.25 to about 20 days, typically is about one to about ten days and preferably is about one to about seven days, at a temperature ranging from about 100° C. to about 250° C., preferably about 125° C. to about 200° C. The crystallizing material can be stirred or agitated as in a rocker bomb. Preferably, the crystallization temperature is maintained below the decomposition temperature of the organic template compound. Especially preferred conditions are crystallizing at about 165° C. for about five to about seven days. Samples of material can be removed during crystallization to check the degree of crystallization and determine the optimum crystallization time.

The crystalline material formed can be separated and recovered by well-known means such as filtration with aqueous washing. This material can be mildly dried for anywhere from a few hours to a few days at varying temperatures, typically about 50°–225° C., to form a dry cake which can then be crushed to a powder or to small particles and extruded, pelletized, or made into forms suitable for its intended use. Typically, materials prepared after mild drying contain the organic template compound and water of hydration within the solid mass and a subsequent activation or calcination procedure is necessary, if it is desired to remove this material from the final product. Typically, mildly dried product is calcined at temperatures ranging from about 260° C. to about 850° C., and preferably from about 425° C. to about 600° C. Extreme calcination temperatures or prolonged crystallization times may prove detrimental to the crystal structure or may totally destroy it. Generally, there is no need to raise the calcination temperature beyond about 600° C. in order to remove organic material from the originally formed crystalline material. Typically, the molecular sieve material is dried in a forced draft oven at 165° C. for about 16 hours and is then calcined in air in a manner such that the temperature rise does not exceed 125° C. per hour until a temperature of about 540° C. is reached. Calcination at this temperature usually is continued for about 4 to 16 hours.

The original cation in the AMS-1B crystalline borosilicate, if not hydrogen, can be replaced all or in part by ion exchange with other cations including other metal ions and their amine complexes, alkylammonium ions, ammonium ions, hydrogen ions, and mixtures thereof The preferred AMS-1B cation is hydrogen ion to form the HAMS-1B component of the catalyst mixture of this invention.

The HAMS-1B crystalline borosilicate useful in this invention is admixed with or incorporated with an alumina binder. Typically, the borosilicate is incorporated within the binder by blending with a sol of the alumina material and gelling the resulting mixture. These supported compositions are then dried at 100° to 200° C. and thereafter generally calcined at 500°–600° C. The crystalline borosilicate content of the supported compositions can vary anywhere from about 5 to 60 weight percent of the total composition. Preferably they contain about 10 to about 60 weight percent of sieve and more preferably, contain about 10 to about 40 weight percent sieve.

The silica used to support the molybdenum compound which is the second component of the catalyst mixture can be obtained from any one of a number of different sources. Preferably, the silica used has a surface area above about 30 sq m/g.

The amount of molybdenum placed on the silica can vary from about 1 to about 20 weight percent, more preferably about 2 to about 15 weight percent, and most preferably from about 3 to about 10 weight percent molybdenum, calculated as the metal. Soluble compounds of molybdenum such as ammonium molybdate may be used to impregnate the silica, and are generally dissolved in water and used to impregnate the silica by the incipient wetness or other technique as may be understood by one skilled in the art. The resulting molybdenum-containing silica is then dried at about 100° to about 200° C. and calcined at about 500° to about 600° C. before use.

The catalyst mixtures containing alumina-supported HAMS-1B crystalline, borosilicate molecular sieve and molybdenum on silica component can be made by several different methods. The two components can be physically mixed in a mixer with a little distilled water to form a paste which may then be dried at elevated temperature and formulated into catalyst particles of appropriate shape and size. Alternatively, the sieve component and the molybdenum on silica component may be added to an alumina sol and the catalyst mixture gelled with, for example, concentrated ammonia after which it is dried, calcined and formulated into catalyst particles of the appropriate size and shape. The gellation technique of forming the catalyst mixtures is preferred. Preferably, the catalyst mixture contains between about 5 and about 95 weight percent of the molybdenum on silica component based upon the total weight of the mixture, more preferably between about 25 and 75 percent, and most preferably, about 35 and 60 percent.

Isomerization of xylene in the presence of the above-described catalyst mixtures is effected by contact at a temperature between about 300° and about 650° C., and preferably between about 350° and about 600° C. The reaction can take place at atmospheric pressure, but the total pressure is preferably within the approximate range of about 1 atm to about 1000 psig.

Reaction is suitably accomplished utilizing a weight hourly space velocity of between about 0.2 and about 50 and preferably between about 1 and about 25. The space velocity is calculated on the basis of the weight of HAMS-1B sieve on alumina present in the catalyst mixture.

Hydrogen is used in the isomerization process and is generally present in a mol ratio, hydrogen to hydrocarbon, between about 0.5 and about 7, and more preferably between about 1 and about 6.

The following Examples will serve to illustrate certain specific embodiments of the hereindisclosed invention. These Examples should not, however, be construed as limiting the scope of the novel invention as there are many variations which may be made thereon without departing from the spirit of the disclosed invention, as those of skill in the art will recognize.

EXAMPLES

General

Isomerization results were obtained using a 2 ft stainless steel reactor with an i.d. of 0.5 in placed in a salt bath. The catalyst was loosely packed in the reactor with glass beads on either side of the catalyst charge.

EXAMPLE 1

In this Example a physical mixture of molybdenum on silica and alumina-supported HAMS-1B was prepared by physically mixing the two separate portions.

The supported HAMS-1B sieve was prepared as follows. A 120.0 g portion of distilled water was added to 40.0 g of the hydrogen form of AMS-1B. A 1985 g portion of PHF alumina sol from American Cyanamid (8.06 wt % solids) was added and the mixture blended in a homogenizer for approximately 5 min. A 160 ml amount of concentrated ammonium hydroxide was added to gel this mixture, and the gel was blended in a mixmaster for about 5 min. The gelled AMS-1B on alumina was dried at 165° C. for 16 hr. The resulting cake was ground to a powder fine enough to pass through a 100 mesh sieve.

An impregnation solution was prepared by adding 33.13 g of ammonium heptamolybdate to 800.0 g of distilled water. This solution was added to 200.0 g of Cab-O-Sil brand silica in a mixmaster. The impregnated $Mo/SiO_2$ was dried 8 hr at 165° C. and then calcined 12 hr at 82° C. The resulting cake was ground to a powder fine enough to pass through a 100 mesh sieve. This results in a 9.0% $Mo/SiO_2$.

The catalyst mixture was prepared by adding 31.25 g of 9.0% $Mo/SiO_2$ to 93.75 g of alumina-supported HAMS-1B and mixing in a mixmaster. A 154.0 g portion of distilled water was added slowly to the result while stirring them with the mixer until a thick paste was formed. The result was then dried at 165° C. for 16 hr and calcined at 482° C. for 12 hr.

Isomerization results for a catalyst mixture which is 25% of 9% $Mo/SiO_2$, 15% HAMS-1B, and 60% $Al_2O_3$ are shown below in Table 1.

TABLE 1

| Component | Composition in Wt % | |
|---|---|---|
| | FEED | EFFL |
| Light P/N's | 0.009 | 2.008 |
| $C_9$ P/N's | 6.455 | 5.080 |
| Total P/N's | 6.464 | 7.088 |
| Benzene | 0.354 | 1.943 |
| Toluene | 0.850 | 1.287 |
| Ethylbenzene | 9.782 | 7.635 |
| Para-xylene | 8.485 | 19.298 |
| Meta-xylene | 49.687 | 42.274 |
| Ortho-xylene | 22.545 | 18.537 |
| Other | 1.833 | 1.936 |
| T (°F.) | 759 | |
| P (PSIG) | 200 | |
| H/HC | 2.68 | |
| WHSV | 11.46 | |
| % EB Conversion | 21.95 | |
| % Xylene Loss | 0.71 | |
| EB Conversion/ % Xylene Loss | 30.88 | |
| % $C_9$ P/N Conversion | 21.31 | |
| % EB Converted to Benzene and Ethane | 82.73 | |
| % Para-xylene Equilibrium Approach | 104.41 | |

EXAMPLE 2

In this Example a physical mixture of molybdenum on silica and alumina-supported HAMS-1B was prepared by physically mixing the two separate portions.

The supported HAMS-1B sieve was prepared as follows. A 120.0 g portion of distilled water was added to 40.0 g of the hydrogen form of AMS-1B. A 1985 g portion of PHF alumina sol (8.06 wt % solids) was added to this mixture and was blended in a homogenizer for approximately 5 min. A 160 ml amount of concentrated ammonium hydroxide was added to gel the mixture, and the gel was blended in a mixmaster for about 5 minutes. The gelled HAMS-1B on alumina was dried at 165° C. for 16 hr and calcined at 510° C. for 12 hr. The resulting cake was ground to a powder fine enough to pass through a 100 mesh sieve.

An impregnation solution was prepared by adding 11.04 g of ammonium heptamolybdate to 800.0 g of distilled water. This solution was added to 200.0 g of silica in a mixmaster. The impregnated $Mo/SiO_2$ was dried at 165° C. for 8 hr and then calcined at 538° C. for 12 hr. The resulting cake was ground to a powder fine enough to pass through a 100 mesh sieve. This results in a 3% $Mo/SiO_2$ material The catalyst mixture was prepared by combining 93.75 g of the 3.0% $Mo/SiO_2$ and 31.25 g of alumina-supported HAMS-1B and mixing in a mixmaster. A 203.0 g portion of distilled water was added slowly to the powders while stirring them with a mixer until a thick paste was formed. The result dried at 165° C. for 16 hr and calcined at 482° C. for 12 hr.

Isomerization results for a catalyst mixture which is 75% of 3% $Mo/SiO_2$, 5% HAMS-1B, and 20% $Al_2O_3$ are shown below in Table 2.

TABLE 2

| Component | Composition in Wt % | |
|---|---|---|
|  | FEED | EFFL |
| Light P/N | 0.008 | 3.519 |
| C9 P/N's | 6.445 | 3.828 |
| Total P/N | 6.453 | 7.347 |
| Benzene | 0.337 | 1.828 |
| Toluene | 0.842 | 1.512 |
| Ethylbenzene | 9.778 | 7.712 |
| Para-xylene | 8.485 | 19.136 |
| Meta-xylene | 49.700 | 41.912 |
| Ortho-xylene | 22.568 | 18.416 |
| Other | 1.837 | 2.137 |
| T (°F.) | 760 | |
| P (PSIG) | 200 | |
| H/HC | 2.76 | |
| WHSV | 5.94 | |
| % EB Conversion | 21.13 | |
| % Xylene Loss | 1.57 | |
| EB Conversion/ % Xylene Loss | 13.46 | |
| % C9 P/N Conversion | 40.61 | |
| % of EB Converted to Benzene and Ethane | 80.93 | |
| % Para-xylene Equilibrium Approach | 104.4 | |

EXAMPLE 3

In this Example a co-gelled mixture of molybdenum on silica and HAMS-1B supported on alumina was prepared. An impregnation solution was prepared by adding 73.61 g of ammonium heptamolybdate to 800 g of distilled water. This solution was added to 200.0 g of silica. The impregnated catalyst was dried 8 hr at 165° C. and then calcined at 510° C. for 4 hr. The resulting cake was ground to a powder fine enough to pass through a 100 mesh sieve.

A 40.0 g portion of distilled water was added to 18.8 g of the hydrogen form of AMS-1B. A 915.0 g portion of PHF alumina sol (8.2 wt % solids) was added and the mixture was blended in a homogenizer for approximately 5 minutes. A 31.0 g portion of the $Mo/SiO_2$ was added to the HAMS-1B/alumina while mixing. A 75 ml amount of concentrated ammonium hydroxide was added to gel this mixture, and the gel was blended in a mixmaster for about 5 minutes. The gelled catalyst was dried at 165° C. for 16 hr, ground to 18/40 mesh, and calcined at 482° C. for 12 hr.

Isomerization results for a catalyst mixture which is 25% of 20% $Mo/SiO_2$, 15% HAMS-1B and 60% $Al_2O_3$ are set forth in Table 3 below.

TABLE 3

| Component | Composition in Wt % | |
|---|---|---|
|  | FEED | EFFL |
| Light P/N | 0.009 | 2.372 |
| C9 P/N's | 6.495 | 4.944 |
| Total P/N | 6.504 | 7.316 |
| Benzene | 0.361 | 1.874 |
| Toluene | 0.856 | 1.303 |
| Ethylbenzene | 9.746 | 7.691 |
| Para-xylene | 8.480 | 19.252 |
| Meta-xylene | 49.666 | 42.185 |
| Ortho-xylene | 22.565 | 18.544 |
| Other | 1.822 | 1.835 |
| T (°F.) | 760 | |
| P (PSIG) | 200 | |
| H/HC | 2.75 | |
| WHSV | 20.48 | |
| % EB Conversion | 21.09 | |
| % Xylene Loss | 0.83 | |
| EB Conversion/ % Xylene Loss | 25.30 | |
| % C9 P/N Conversion | 23.88 | |
| % of EB Converted to Benzene and Ethane | 83.49 | |
| % Para-xylene Equilibrium Approach | 104.28 | |

EXAMPLE 4

In this Example a co-gelled mixture of molybdenum on silica and HAMS-1B supported on alumina was prepared. An impregnation solution was prepared by adding 33.13 g of ammonium heptamolybdate to 800 g of distilled water. This solution was added to 200.0 g of silica. The impregnated catalyst was dried 8 hr at 165° C. and then calcined at 510° C. for 4 hr. The resulting cake was ground to a powder fine enough to pass through a 100 mesh sieve.

A 40.0 g portion of distilled water was added to 18.8 g of the hydrogen form of AMS-1B. A 915.0 g portion of PHF alumina sol (8.2 wt % solids) was added and this mixture was blended in a homogenizer for approximately 5 minutes. A 31.0 g portion of the $Mo/SiO_2$ component was added to the HAMS-1B on alumina component while mixing. A 75 ml amount of concentrated ammonium hydroxide was added to gel this mixture, and the gel was blended in a mixmaster for about 5 minutes. The gelled catalyst mixture was dried at 165° C. for 16 hr, ground to 18/40 mesh, and calcined at 482° C. for 12 hr.

Isomerization results for a catalyst mixture which is 40% of 9% Mo/SiO$_2$, 15% HAMS-1B, and 60% Al$_2$O$_3$ are set forth in Table 4 below.

TABLE 4

| Component | Composition in Wt. % | |
|---|---|---|
| | FEED | EFFL |
| Light P/N | 0.015 | 2.427 |
| C$_9$ P/N's | 6.514 | 4.667 |
| Total P/N | 6.529 | 7.094 |
| Benzene | 0.366 | 1.735 |
| Toluene | 0.859 | 1.358 |
| Ethylbenzene | 9.743 | 7.816 |
| Para-xylene | 8.480 | 19.260 |
| Meta-xylene | 49.656 | 42.187 |
| Ortho-xylene | 22.551 | 18.702 |
| Other | 1.816 | 1.848 |
| T (°F.) | 761 | |
| P (PSIG) | 200 | |
| H/HC | 2.70 | |
| WHSV | 15.12 | |
| % EB Conversion | 19.78 | |
| % Xylene Loss | 0.67 | |
| EB Conversion/ % Xylene Loss | 29.72 | |
| % C$_9$ P/N Conversion | 28.35 | |
| % of EB Converted to Benzene and Ethane | 82.17 | |
| % Para-xylene Equilibrium Approach | 103.99 | |

What is claimed is:

1. A vapor phase process comprising isomerizing in the presence of hydrogen an unextracted xylene stream containing a major amount of xylene and a minor amount of ethylbenzene to a mixture rich in paraxylene over a catalyst mixture containing a supported HAMS-1B crystalline, borosilicate molecular sieve incorporated into alumina component and a molybdenum on silica component, said molybdenum on silica component containing between about 1 and about 20 weight percent molybdenum calculated as the metal, said catalyst mixture containing between about 5 and about 95 percent by weight of said molybdenum on silica component based upon the total weight of said mixture, and said HAMS-1B crystalline, borosilicate molecular sieve incorporated in alumina component containing between about 40 and about 95 weight percent alumina.

2. The process of claim 1 wherein said molybdenum on silica component contains between about 2 and about 15 weight percent molybdenum.

3. The process of claim 2 wherein said catalyst mixture contains between about 25 and 75 percent by weight of said molybdenum on silica component.

4. The process of claim 3 wherein said HAMS-1B crystalline borosilicate molecular sieve incorporated in alumina component contains between about 40 and about 90 weight percent alumina.

5. The process of claim 1 wherein said molybdenum on silica component contains between about 3 and about 10 weight percent molybdenum.

6. The process of claim 5 wherein said catalyst mixture contains between about 35 and 60 percent by weight of said molybdenum on silica component.

7. The process of claim 6 wherein said HAMS-1B crystalline borosilicate molecular sieve incorporated in alumina component contains between about 60 and about 90 weight percent alumina.

* * * * *